US008980567B2

(12) United States Patent
Demchyshyn et al.

(10) Patent No.: US 8,980,567 B2
(45) Date of Patent: *Mar. 17, 2015

(54) EX VIVO METHOD FOR DETERMINING POTENTIAL GLP-2 RECEPTOR MODULATORS

(71) Applicant: NPS Pharmaceuticals, Inc., Bedminster, NJ (US)

(72) Inventors: Lidia L. Demchyshyn, Toronto (CA); Hong Wang, Hamilton (CA)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,822

(22) Filed: Jun. 5, 2013

(65) Prior Publication Data
US 2014/0024065 A1 Jan. 23, 2014

Related U.S. Application Data

(62) Division of application No. 13/565,618, filed on Aug. 2, 2012, now Pat. No. 8,481,276, which is a division of application No. 13/154,071, filed on Jun. 6, 2011, now Pat. No. 8,257,983, which is a division of application No. 12/358,123, filed on Jan. 22, 2009, now Pat. No. 7,977,061, which is a division of application No. 11/607,030, filed on Dec. 1, 2006, now Pat. No. 7,498,141.

(60) Provisional application No. 60/741,075, filed on Dec. 1, 2005.

(51) Int. Cl.
*G01N 33/567* (2006.01)
*G01N 33/50* (2006.01)
*G01N 33/74* (2006.01)

(52) U.S. Cl.
CPC ........ *G01N 33/5088* (2013.01); *G01N 33/5082* (2013.01); *G01N 33/74* (2013.01); *G01N 2333/605* (2013.01); *G01N 2333/726* (2013.01); *G01N 2500/04* (2013.01)
USPC ......................................... 435/7.21; 436/503

(58) Field of Classification Search
None
See application file for complete search history.

(56) References Cited

U.S. PATENT DOCUMENTS

2002/0123461 A1 9/2002 Drucker et al.

FOREIGN PATENT DOCUMENTS

WO WO 9803547 1/1998
WO WO 2007119101 10/2007

OTHER PUBLICATIONS

Boushey R. et al, "GLP-2 Decreases Mortality and Reduces the Severity' of Indomethacininduced Murine Enteritis", Am J. Physiol. 1999; vol. 277 pp. E937-E947.
Drucker D.J. et al, "Human [Gly2] GLP-2 Reduces the Severity of Colonic Injury in a Murine Model of Experimental Colitis", Am. J. Physiol. 1999; vol. 276 pp. G79-G91.
Office Action issued in U.S. Appl. No. 12/358,123 dated Oct. 27, 2010.
Prasad R. et al, "Glucagon-like Peptide-2 Analogue enhances Intestinal Mucosal Mass After Ischemia and Reperfusion", J: Pediatr. Sur.. 2000; vol. 35 ws. 357-9.
Yusta B. et al, "The Glucagon-like Peptide-2 Receptor Mediates Direct Inhibition of Cellular Apoptosis via a cAMP-dependent Protein Kinase-Independent Pathway", J. Biol. Chem. 2000; vol. 275 pp. 35345-35352.
Alavik, et al., "Treatment of inflammatory bowel disease in a rodent model with the intestinal growth factor glucagon-like peptide-2", J. Ped. Surg. 2000, vol. 35, 847-51.
Benjamin, M.A. et al, "Glucagon-like Peptide-2 Enhances Intestinal Epithelial Barrier Function of Both Transcellular and Paracellular Pathways in the Mouse", Gut 2000; vol. 47 pp. 112-119.
Boushey R. et al, "GLP-2 Decreases Mortality and Reduces the Severity' of Indomethacin-induced Murine Enteritis", Am J. Physiol. 1999; vol. 277 pp. E937-E947.
Boushey, et al., "Glucagon-like peptide (GLP)-2 reduces chemotherapy-associated mortality and enhances survival in cells expressing a transfected GLP-2 receptor", Cancer Research, 2001, vol. 61, 687-93.
Brubaker, P.L. et al, "Intestinal Function in Mice With Small Bowel Growth Induced by Glucagon-like Peptide-2", Am. J. Physiol. 1997, vol. 272 pp. E1050-E1058.
Burin D.G. et al, "GLP-2 Stimulates Intestinal Growth in Premature TPN-fed Pigs by Suppressing Proteolysisrand Apoptosis", Am. J. Physiol. 2000; vol. 279 pp. G1249-G1256.
Cameron H. et al, Glucagon-like Peptide-2—Enhanced Barrier Function Reduces Pathophysiology in a Model of Food Allerg., Am. J. Physiol. 2003, vol. 284, G905-G912.
Chance W.T. et al, "Maintaining Gut Integrity During Parenteral Nutrition of Tumor-Bearing Rats: Effects of Glucagon-like Peptide 2", Nutrition and Cancer 2000; vol. 37 pp. 215-222.
Chance W.T. et al, "Prevention of Parenteral Nutrition-induced Gut Hypoplasia by Coinfusion of Gluca 4 on-like Pe.tide-2", Amer. J. Ph siol. 1997; vol. 273 ws G559-63.
Cheeseman C.I., "The Effect of Gastric Inhibitory Polypeptide and Glucagon Like Peptides on Intestinal Hexose Transport", Am. J. Physiol. 1996; vol. 271 pp. G477-G482.
Cheeseman C.I., "Upregulation of SGLT-1 Transport Activity in Rat Jejunum Induced by GLP-1 Infusion in vivo", Am. J. Physiol. 1997; vol. 273 pp. R1965-R1971.
Drucker, D.J. et al, "Induction of Intestinal Epithelial Proliferation by Glucagon-like Peptide-2", Proc. Natl. Acad. Sci. USA 1996; vol. 93 pp. 7911-7916.
Drucker D.J. et al, "Human [Gly2] GLP-2 Reduces the Severiry of Colonic Injury in a Murine Model of Experimental Colitis", Am. J. Physiol. 1999; vol. 276 pp. G79-G91.
Guan X. et al, "GLP-2 Mediated Up-Regulation of Intestinal Blood Flow and Glucose Uptake Is Nitric Oxide-Dependent in TPN-Fed Piglets", Gastroenterol 2003, vol. 125 pgs.
International Preliminary Report on Patentability and Writton Opinion issued in International Application No. PCT/IB2006/003943 dated Dec. 17, 2007.

(Continued)

*Primary Examiner* — Robert Landsman
(74) *Attorney, Agent, or Firm* — Stoel Rives LLP

(57) ABSTRACT

Disclosed herein is a method for measuring the contractility of intestinal tissue upon treatment with GLP-2 or a GLP-2 ligand. Also disclosed is an assay which directly measures the activity of GLP-2 or GLP-2 ligands ex vivo and permits the screening of putative GLP-2 ligands in native tissue.

16 Claims, 8 Drawing Sheets

(56) References Cited

OTHER PUBLICATIONS

International Search Report issued in International Application No. PCT/IB2006/003943 dated Dec. 17, 2007.

Kouris, et al., "The effect of glucagon-like peptide 2 on intestinal permeability and bacterial translocation in acute nectrotizing pancreatitis", Am. J. Surg., 2001, vol. 181, 571-575.

Lovshin J.A. et al, "Extrahypothalimic Expression of the Glucagon-like Peptide-2 (GLP-2) Receptor is Coupled to Reduction of Glutamate-induced Cell Death in Cultured Hippocampal Cells", Endocrinoloy 2004; vol. 145 pp. 3495-3506.

Monroe D.G. et al, "Prototypic G Protein-Coupled Receptor for the Intestinotrophic Factor Glucagon-like Peptide-2", Proc. Natl Acad. Sci USA 1999; vol. 96 pp. 1569-1573.

Office Action issued in U.S. Appl. No. 11/607,030 dated Mar. 18, 2008.

Office Action issued in U.S. Appl. No. 12/358,123 dated Jul. 14, 2010.

Office Action issued in U.S. Appl. No. 12/358,123 dated Dec. 27, 2010.

Office Action issued in U.S. Appl. No. 13/154,071 dated Jan. 23, 2012.

Office Action issued in U.S. Appl. No. 13/565,618 dated Oct. 15, 2012.

Notice of Allowance issued in U.S. Appl. No. 11/607,030 dated Oct. 22, 2008.

Notice of Allowance issued in U.S. Appl. No. 12/358,123 dated Mar. 7, 2011.

Notice of Allowance issued in U.S. Appl. No. 13/154,071.

Prasad R. et al, "GLP-2 Accelerates Recovery of Mucosal Absorptive Function After Ischemia/Reperfusion", J. Pediatr. Surg. 2001; vol. 36 pp. 570-572.

Prasad R. et al, "Glucagon-like Peptide-2 Analogue enhances Intestinal Mucosal Mass After Ischemia and Re•erfusion", J: Pediatr. Sur.. 2000; vol. 35 ws. 357-9.

Preliminary Amendment filed in U.S. Appl. No. 13/673,386 dated Oct. 11, 2013.

Ramsanahie A.P. et al, "Glucagon-like Peptide 2 Enhances Intestinal Epithelial Restitution", J. Surg Res 2002; vol. 107 pp. 44-49.

Response to Office Action filed in U.S. Appl. No. 11/607,030 filed Sep. 18, 2008.

Response to Office Action filed in U.S. Appl. No. 12/358,123 filed Dec. 14, 2010.

Response to Office Action filed in U.S. Appl. No. 12/358,123 filed Feb. 25, 2011.

Response to Office Action filed in U.S. Appl. No. 13/154,071 dated Apr. 20, 2012.

Response to Office Action filed in U.S. Appl. No. 13/565,618 dated Feb. 15, 2013.

Scott, et al., "GLP-2 augments the adaptive response to massive intestinal resection in rat", Am. J. Physio. 1998, vol. 275, G911-921.

Shibata, et al., "Effect of glucagon, glicentin, glucagon-like peptide-1 and -2 on interdigestive gastroduodenal motility in dogs with a vagally denervated gastric pouch", Scandinavian Journal of Gastroenterology, 36(10), 2001, 1049-1055.

Shin, et al., "Mucosal adaptation to enteral nutrients is dependent on the physiologic actions of glucagon-like peptide-2 in mice", Gastroenterology, 128(5), 2005, 1340-1353.

Sigalet D.L. et al, "Hormonal Therapy for Short Bowel Syndrome", J. Pediatr. Surg. 2000; vol. 35 pp. 360-364.

Tavakkolizadeh A., et al, "Glucagon-like Peptide 2: A New Treatment for Chemotherapy-Induced Enteritis", J. Surg. Res. 2000; vol. 91 pp. 77-82.

Tsai, C.H. et al, "Biological Determinants of Intestinotrophic Properties of GLP-2 in vivo", Am. J. Physiol. 1997; vol. 272 pp. G662-G668.

Tsai, C.H. et al, "Intestinal Growth-Promoting Properties of Glucagon-like Peptide-2 in Mice", Am. J. Physiol. 1997; vol. 273 pp. E77-E84.

Walsh N.A. et al, "Glucagon-like Peptide-2 Receptor Activation in the Rat Intestinal Mucosa", Endocrinology 2003; vol. 144(10) pp. 4385-4392.

Wojdemann, M. et al, "Glucagon-like Peptide-2 Inhibits Centrally Induced Antral Motility in Pigs", Scand. J. Gastroenterol. 1998; vol. 33 pp. 828-832.

Wojdemann, M. et al, "Inhibition of Sham Feeding-stimulated Human Gastric Acid Secretion by Glucagon-like Peptide-2", J. Clin Endocrinol Metab., 1999; vol. 84 pp. 2513-2517.

Xiao, Q. et al, "Secretion of the Intestinotrophic Hormone Glucagon-like Peptide 2 is Differentially Regulated by Nutrients in Humans", Gastroenterol 1999; vol. 117 pp. 99-105.

Yusta B. et al, "Ideptification of Glucagon-like Peptide-2 (GLP-2)-Activated Signaling Pathways in Baby Hamster Kidney Fibroblasts Expressing the Rat GLP-2 Receptor", J. Biol. Chem. 1999, vol. 274 pp. 30459-30467.

EX VIVO METHOD FOR DETERMINING POTENTIAL GLP-2 RECEPTOR MODULATORS

CROSS-REFERENCE TO RELATED APPLICATION

This application is a divisional of U.S. patent application Ser. No. 13/565,618, filed on Aug. 2, 2012, which issued as U.S. Pat. No. 8,481,276 on Jul. 9, 2013, which is a divisional of U.S. patent application Ser. No. 13/154,071, filed on Jun. 6, 2011, which issued as U.S. Pat. No. 8,257,983 on Sep. 4, 2012, which is a divisional application of U.S. patent application Ser. No. 12/358,123 filed on Jan. 22, 2009, which issued as U.S. Pat. No. 7,977,061 on Jul. 12, 2011, which is a divisional application of U.S. patent application Ser. No. 11/607,030, filed on Dec. 1, 2006, which issued as U.S. Pat. No. 7,498,141 on Mar. 3, 2009, which claims priority under 35 U.S.C. §119(e) to U.S. Provisional Application Ser. No. 60/741,075, filed on Dec. 1, 2005, the entire contents of each of which are hereby incorporated by reference.

BACKGROUND OF THE INVENTION

Glucagon-like peptide-2 (GLP-2) is a 33-amino acid proglucagon-derived peptide secreted by the endocrine L-cell primarily in the lower gastrointestinal tract in response to luminal nutrients. Plasma levels have been shown to significantly increase within an hour of ingesting a meal, in particular following the ingestion of carbohydrates or fat (1). GLP-2 has been shown to be responsible for the regulation of proliferation and apoptosis of the intestinal epithelium (2,3). These changes in part result in an increase in mucosal surface area, enhanced absorptive efficiency and barrier function in the small intestine (4-6). GLP-2 also decreases gastric motility, inhibits gastric acid secretion, increases nutrient transport activity and acutely increases intestinal and portal blood flow (7-11).

GLP-2 and GLP-2 analogues promote the growth and repair of the intestinal epithelium in models of disease, including enhanced adaptation and nutrient absorption following small bowel resection and alleviation of TPN-induced hypoplasia in rodents (12-15). GLP-2 analogues have demonstrated decreased mortality and improvement of disease-related histopathology in animal models of intestinal damage such as indomethacin-induced enteritis, dextran sulfate-induced colitis and chemotherapy-induced mucositis (16-19).

The intestinotrophic effects of GLP-2 are mediated by the GLP-2 receptor (GLP-2R), a member of the superfamily of G-protein coupled receptors and most closely related to the GLP-1 and glucagon receptor gene subfamily (20). The GLP-2R is a high-affinity, ligand-specific functional receptor coupled to the G-protein Gs. Studies of the activation of the cloned GLP-2R by GLP-2 analogues show a correlation of in vitro activity with in vivo intestinotrophic efficacy (20).

To date, characterization of GLP-2R function has been limited to heterologous cell line expression, mucosal fractions and primary cell cultures. GLP-2 selectively stimulates cAMP production in recombinantly expressing GLP-2R cell lines, isolated intestinal mucosal fractions containing enteroendocrine and neural cells and primary hippocampal cultures (21-24). The study of native GLP-2R biological activity has focused on in vivo animal models and ex vivo model systems that require exogenous application of GLP-2 to the whole animal prior to tissue isolation (2-19, 25-31). There is no ex vivo method for characterizing putative GLP-2 ligands directly; such a method would have obvious utility, for example in the screening and characterization of GLP-2 ligands of pharmaceutical interest.

SUMMARY OF THE INVENTION

Disclosed herein is a method for measuring the contractility of intestinal tissue upon treatment with GLP-2 or a GLP-2 ligand. Thus, one aspect of the invention is an assay which directly measures the activity of GLP-2 or GLP-2 ligands. Another aspect of the invention is the direct characterization of the GLP-2 receptor. A further aspect of the invention is a method for screening compounds for activity at the GLP-2 receptor, such as putative GLP-2 agonists, antagonists, modulators or the like.

DETAILED DESCRIPTION OF THE INVENTION

Figure 1:
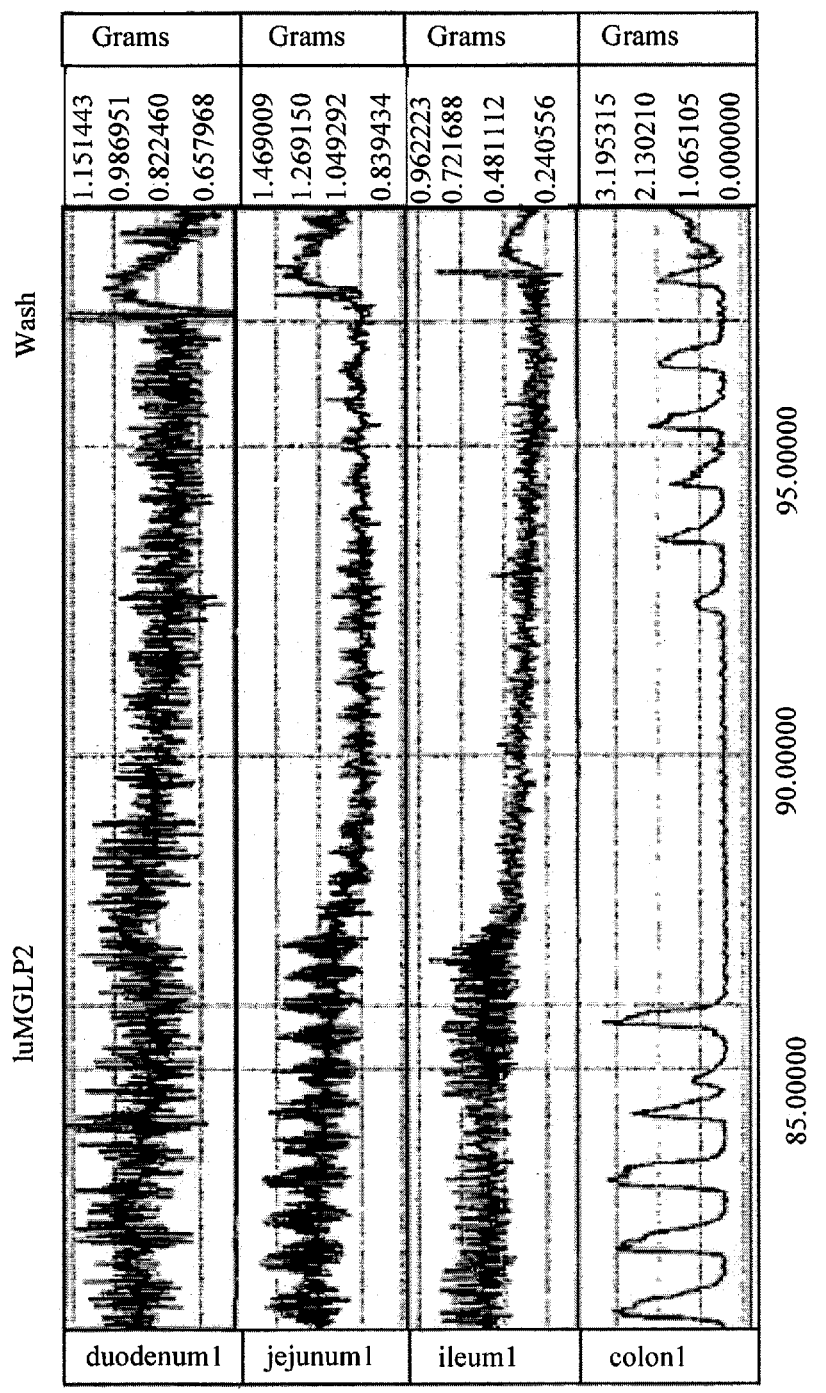
FIG. 1 shows the organ bath trace of the effect of 1uM GLP-2(1-33) on rat contractility in duodenum, jejunum, ileum and colon.

Definitions hGLP-2R is the human GLP-2 receptor; rGLP-2R is the rat GLP-2 receptor. hGLP-2 is human GLP-2 (also known as Teduglutide); rGLP-2 is rat GLP-2.

A "GLP-2 ligand" is defined as any molecule which interacts with the GLP-2 receptor; such molecules may be peptides (such as analogues of naturally occurring GLP-2) or small molecules.

A "modulator" is defined as a molecule which modulates the activity of a GLP-2 agonist.

"Intestinal tissue" is broadly defined as intestine from the pylorus to the rectum. "Small intestine" is defined as intestine from the pylorus to the ileo-cecal valve (it may also be defined as duodenum, jejunum and ileum). "Large intestine" is defined as intestine distal from the cecum (it may also be defined as colon tissue).

Disclosed herein is an assay which, for the first time, demonstrates the ability of GLP-2 receptor ligands to directly affect native GLP-2R-mediated effects in colon tissue ex vivo. As a result, it is possible to directly screen and pharmacologically characterize GLP-2 ligands, such as peptidic analogies of GLP-2, as well as small molecule agonists, antagonists and modulators, against whole tissue.

Such tissue is of mammalian origin; in one aspect it is of rat origin, in others it is of mouse or guinea-pig origin.

The assay method comprises measuring the contractility of segments of intestinal tissue ex vivo. The fact that this assay is useful for the stated purpose is not obvious, based upon the known expression levels of the GLP-2 receptor in this tissue. Further, previous studies have shown that direct application of GLP-2 ex vivo to this tissue has no effect.

One aspect of the invention is a method for characterizing the GLP-2 receptor; for example in an endeavour to better understand the physiological role of GLP-2 and the GLP-2 receptor in intestinal tissue or to elucidate the role of putative mediators related to GLP-2 activation and physiology.

Another aspect of the invention is a method for determining whether a compound is active on the GLP-2 receptor comprising the step of measuring contractility of intestinal tissue segments ex vivo in the presence and absence of compound, wherein a difference in contractility in the presence of the compound is indicative of activity on the GLP-2 receptor.

Yet another aspect of the invention is a method for determining whether a compound acts as a GLP-2 receptor agonist comprising the step of measuring contractility of intestinal tissue segments ex vivo in the presence and absence of compound, wherein inhibition of contractility in the presence of the compound is indicative of GLP-2 receptor agonist activity.

Yet another aspect of the invention is a method for determining whether a compound acts as a GLP-2 receptor antagonist comprising the step of measuring the effect of a GLP-2 receptor agonist on contractility of intestinal tissue segments ex vivo in the presence and absence of the compound, wherein a decrease of agonist inhibition of contractility in the presence of the compound is indicative of GLP-2 receptor antagonist activity.

Another aspect of the invention is a method of assaying compounds for activity at the GLP-2 receptor comprising the steps of
  i. Obtaining a segment of intestinal tissue,
  ii. Suspending the segment in an organ bath,
  iii. Placing the segment under tension,
  iv. Incubating the segment with a compound of interest and
  v. Measuring the contractility of the tissue; wherein an effect on contractility of the segment is indicative of activity on the GLP-2 receptor.

Figure 2:
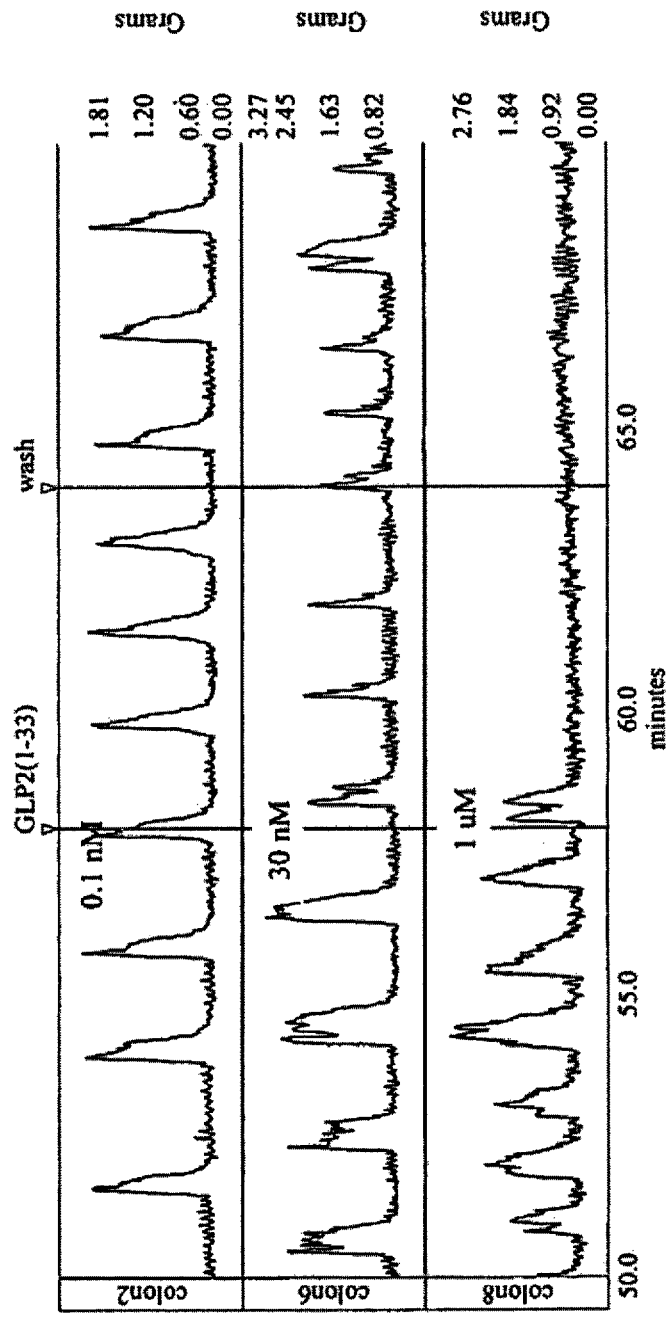
FIG. 2 shows the organ bath trace of the effect of GLP-2 (1-33) on rat colon contractility.
Figure 3:
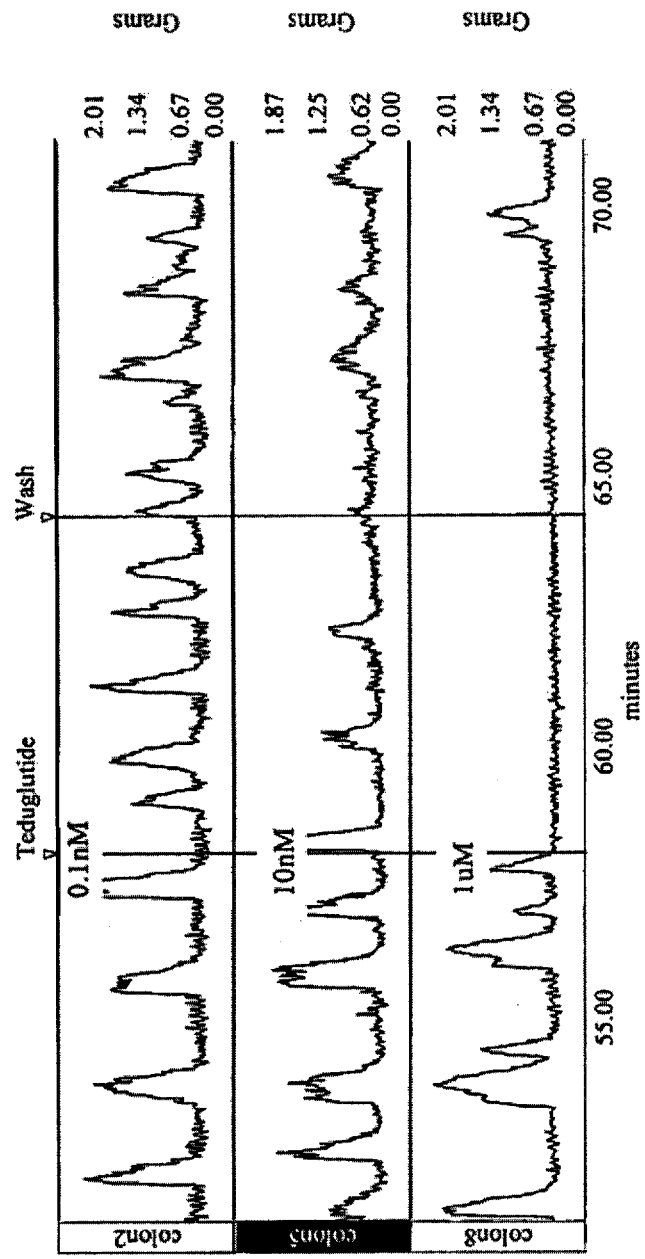
FIG. 3 Shows the organ bath trace of the effect of [gly2] GLP-2 on rat colon contractility.

In one aspect the tissue is intestinal tissue. In another it is small intestine tissue. In yet another it is large intestine tissue or colon tissue. FIG. 1 shows the Organ Bath Trace of the effect of 1uM GLP-2(1-33) on rat contractility in duodenum, jejunum, ileum and colon. FIG. 2 shows that GLP-2(1-33) inhibits spontaneous colon contractility in a concentration-dependent manner in rat colon tissue; FIG. 3 shows the analogous effect of Teduglutide.

Figure 4:
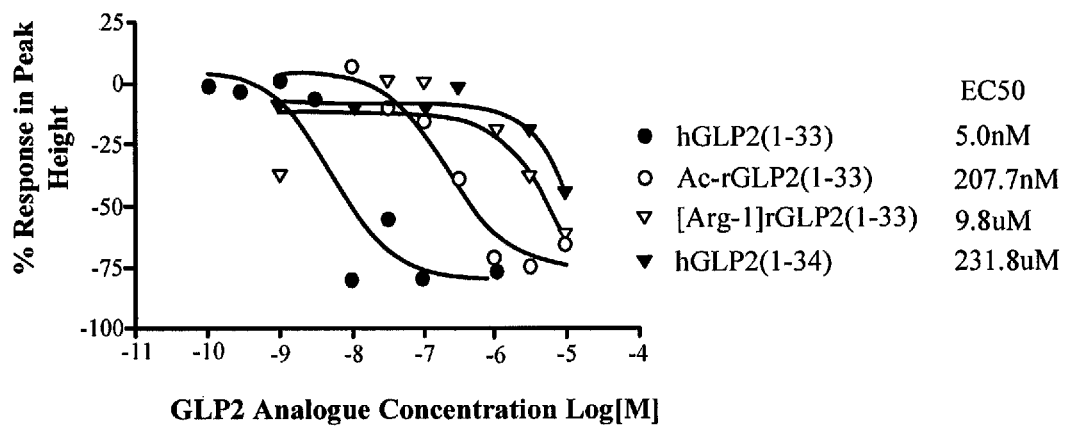
FIG. 4 shows the inhibitory effects of GLP-2 analogues on spontaneous contractility in rat colon.
Figure 4:
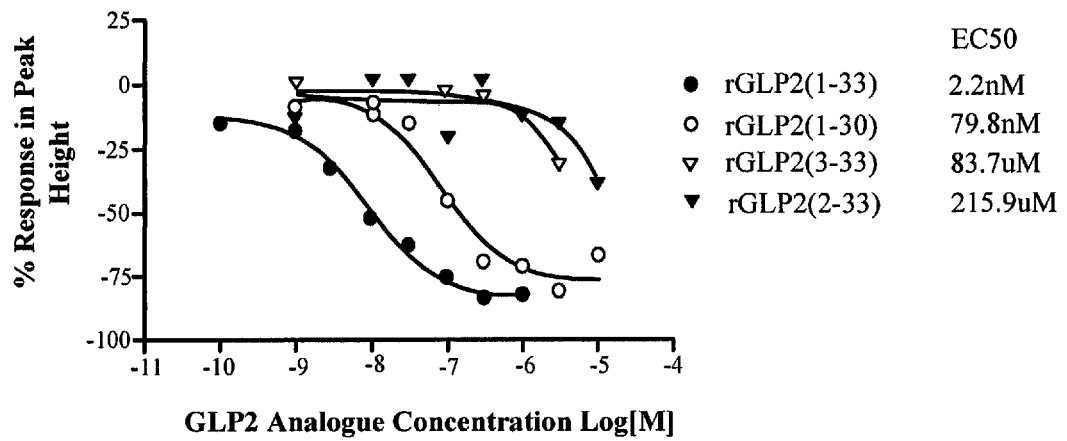
Figure 5:
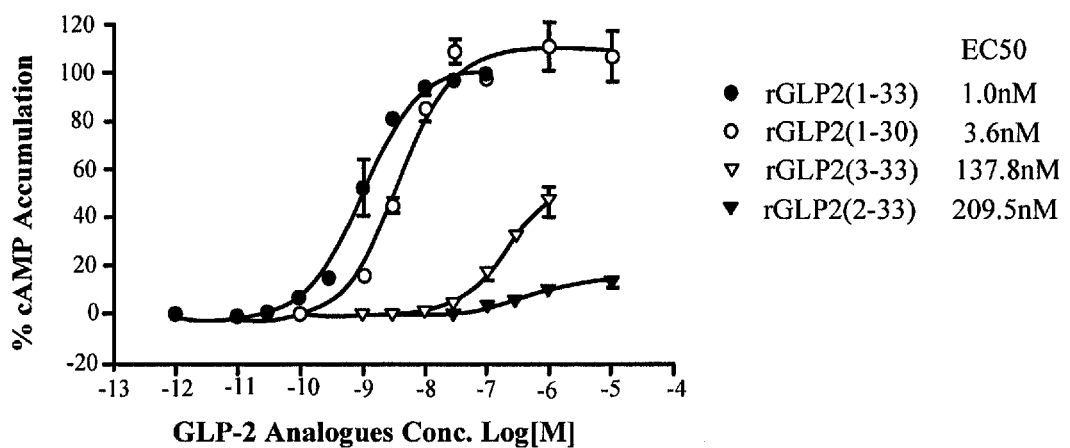
FIG. 5 shows the effect of GLP-2 analogues on cAMP accumulation in EBNA293 cells stably expressing rat GLP-2R.
Figure 5:
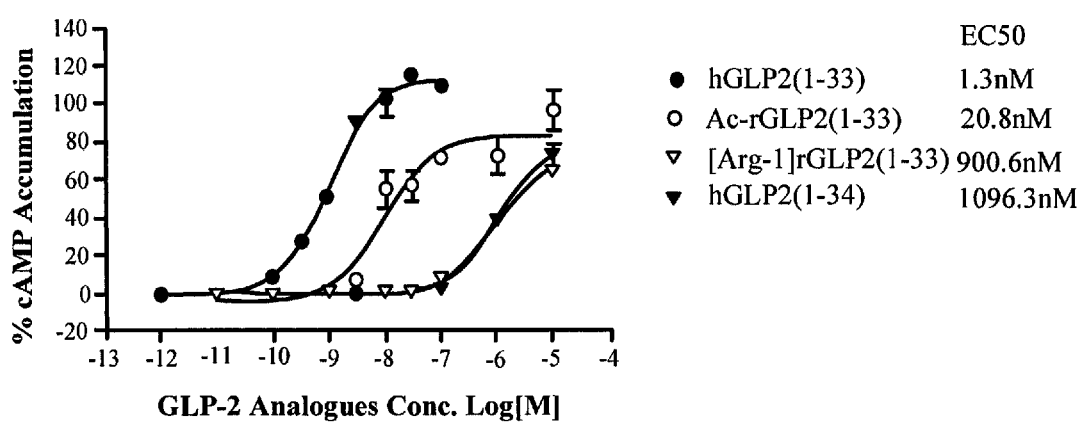

The assay of putative agonists may be conducted by incubation of the colon segments with a predetermined concentration of the ligand to be tested for 5 to 10 minutes. FIG. 4 shows typical results for a number of GLP-2 analogues. FIG. 5 shows the effect of GLP-2 analogues on cAMP accumulation in EBNA293 cells stably expressing rGLP-2R.

Figure 6:
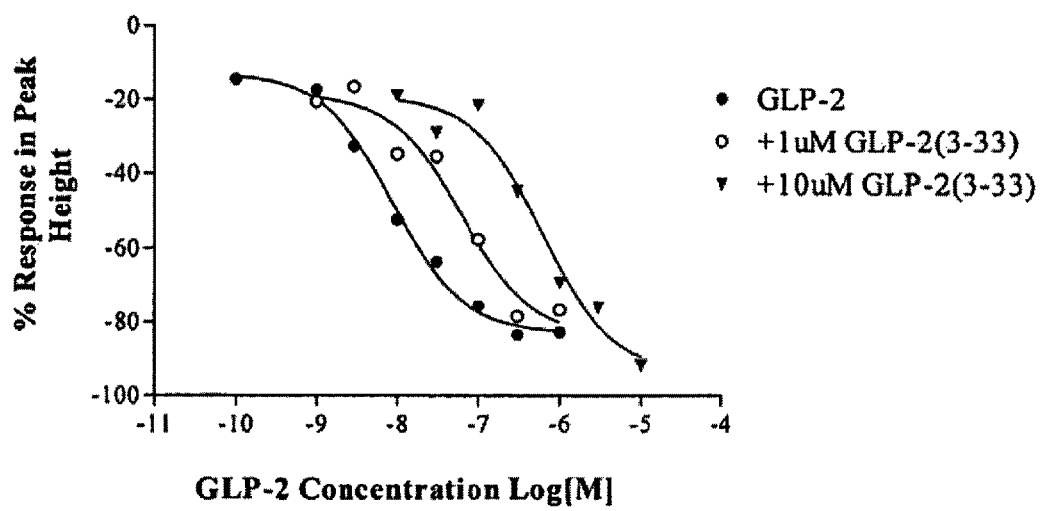
FIG. 6 shows the effect of GLP-2(3-33) on GLP-2(1-33)-induced inhibition of colon contractility.
Figure 7:
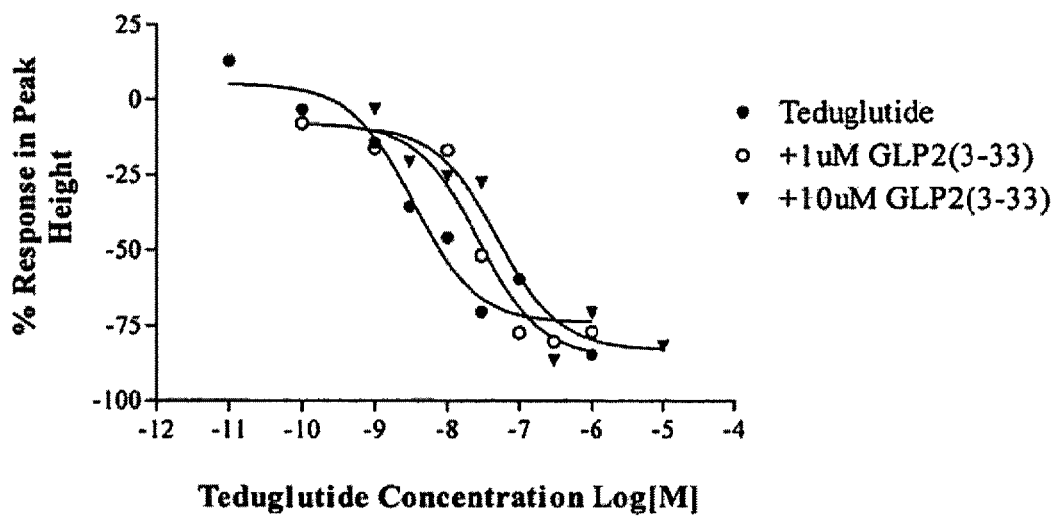
FIG. 7 shows the effect of GLP-2(3-33) on teduglutide-induced inhibition of rat colon contractility.
Figure 8:
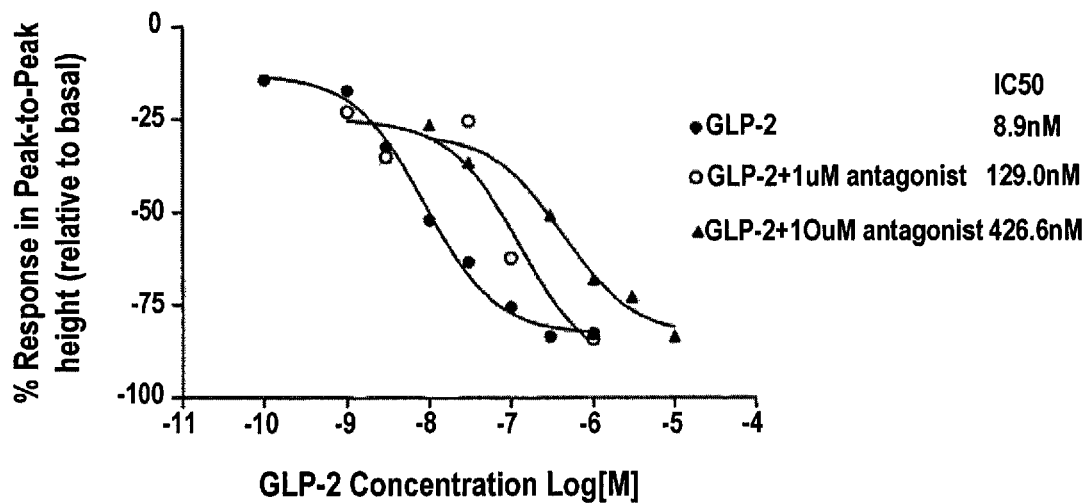
FIG. 8 shows the effect of a small molecule antagonist on GLP-2(1-33)-induced inhibition of colon contractility.

The assay of putative antagonists may be conducted by pre-incubation of the colon segments with a predetermined concentration for, for example, 5 to 10 minutes of the ligand to be tested followed by addition and incubation of a predetermined concentration of a GLP-2 agonist. FIGS. 6, 7 and 8 show typical results for a number of GLP-2 antagonists; concentration-response curves are clearly right-shifted, as expected.

Figure 9:
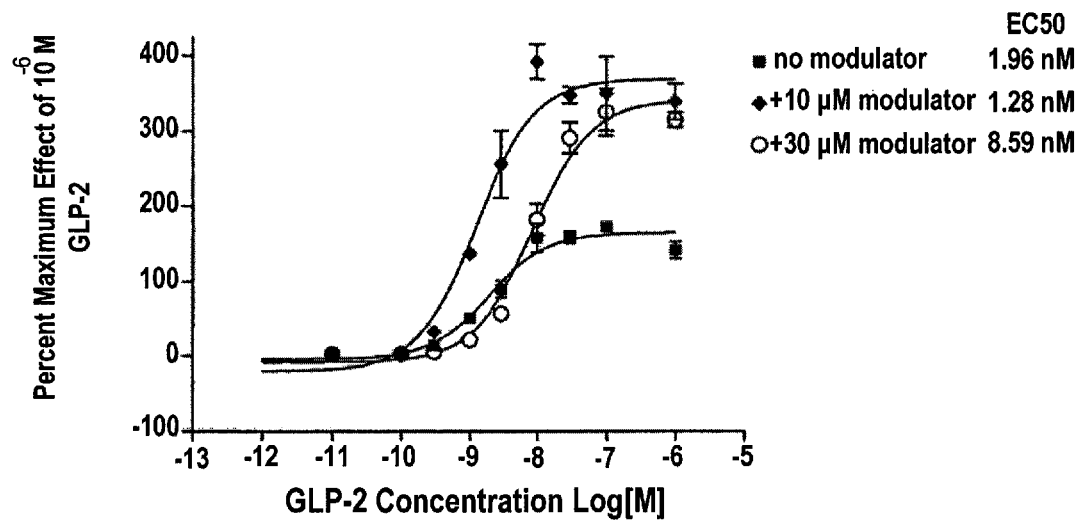
FIG. 9 shows the effect of a small molecule positive modulator on GLP-2(1-33)-induced cAMP accumulation.
Figure 10:
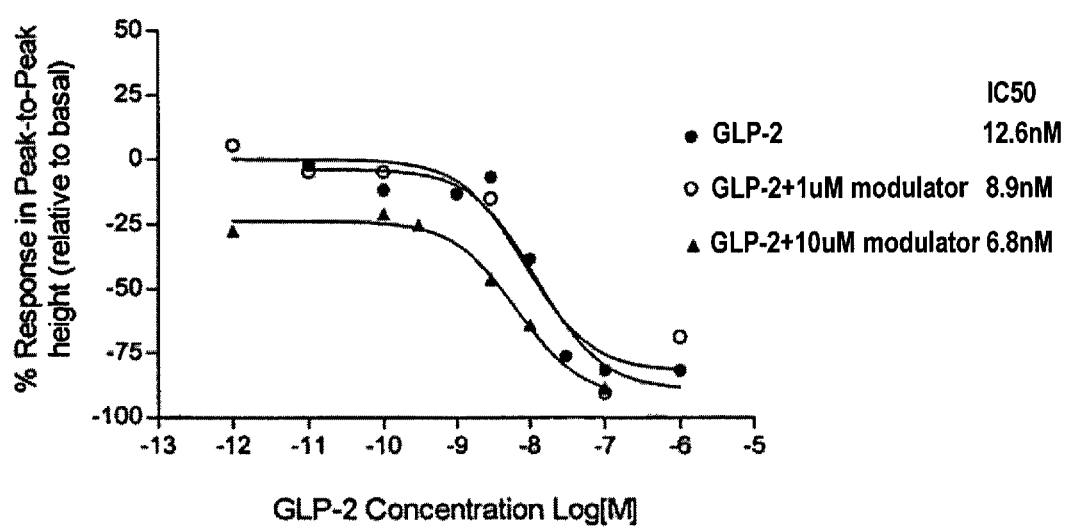
FIG. 10 shows the effect of a small molecule positive modulator on GLP-2(1-33)-induced inhibition of colon contractility.

The assay of putative modulators, may be conducted by pre-incubation of the colon segments with a predetermined concentration of the ligand to be tested for, for example, 5 to 10 minutes followed by the addition and incubation of a pre-determined concentration of a GLP-2 agonist. FIG. 10 show typical results for a GLP-2 positive modulator; the effect of the modulation is clearly demonstrated. FIG. 9 shows the corresponding effect on GLP-2(1-33)-induced cAMP accumulation.

Methods & Results

It should be noted that the methods described below are illustrative in nature, and that the invention is not limited to the particular embodiments described.

Segments of colon from male Sprague Dawley rats were suspended in organ bath chambers containing Krebs' solution and maintained at 37° C. with 95% $O_2$ and 5% $CO_2$. Basal tone, contractility rate and peak height were used to measure the properties of spontaneous and ligand-mediated colonic contractions. Segments were initially loaded to a tension of 2 g and allowed to equilibrate for 60 minutes. During this period, segments were repeatedly washed every 10 minutes. [gly2]GLP-2 ("Teduglutide", a GLP-2 agonist) and GLP-2 analogues were subsequently incubated with each tissue segment for 5 to 10 minutes. The tissues were allowed to re-equilibrate with repeated washes following each experiment.

Teduglutide and GLP-2(1-33) inhibited muscle contractility in a concentration-dependent manner with an estimated $IC_{50}$ of 4.9±1.9 (SE) nM (n=6) and 13.5±5.4 nM (n=9), respectively. While having no effect alone, GLP-2(3-33) (a GLP-2 antagonist/partial agonist) blocked the inhibitory effects of Teduglutide and GLP-2. In the presence of 10 μM GLP-2(3-33), Teduglutide and GLP-2(1-33) inhibited colon contractility with an IC50 of 59.9±11.9 nM (n=6) and 142.7±55.9 nM (n=5) respectively. The rank orders of potency of GLP-2 peptide analogues were similar to that previously reported for their cAMP activation in cell lines recombinantly expressing the rGLP-2R.

These studies demonstrate the ability of GLP-2 to reproducibly and significantly reduce spontaneous contractility of rat colon segments suspended in organ bath chambers. GLP-2-induced inhibition of colon contractility is concentration-dependent and reversible following a wash-out period. The GLP-2R antagonist/partial agonist GLP-2(3-33) blocks the effect of GLP-2(1-33) in a concentration-dependent manner. The rank order of potency of GLP-2 analogues on the inhibition of colon contractility was comparable to the rank order of increased cAMP accumulation in heterologous cells expressing GLP-2R.

Therefore the described assay enables native GLP-2R characterization by the direct application of GLP-2 to intestinal tissue segments ex vivo. As a result, it is possible to screen and pharmacologically characterize GLP-2 peptide analogues, GLP-2R small molecule agonist and antagonists against whole tissue.

Colon Contractility—Methods

Animals

Male Sprague-Dawley (SD) rats (Charles River Canada, Quebec), weighing 200-250 g, were used for these studies. The animals were housed on contact bedding and kept with free access to food (Purina Rodent Diet) and water in a facility with regulated temperature and humidity, under an alternate 12-hour light/dark cycle. Animals were acclimatized for 3-5 days prior to harvesting of tissues.

Tissue Preparation

Rats were euthanized by decapitation. The entire intestine was quickly removed and placed in a Petri dish containing a Sylgard layer and 37° C. Krebs' solution bubbled with 95%

$O_2$ and 5% $CO_2$. The Krebs' solution (pH 7.4) contained 118.1 mM NaCl, 25 mM $NaHCO_3$, 4.7 mM KCl, 1.2 mM $KH_2PO_4$, 1.2 mM $MgSO_4.7H_2O$, 2.5 mM $CaCl_2.2H_2O$ and 11 mM glucose. The colon was isolated, cleaned of superficial fat and mesentery and sectioned into eight 1-cm long segments. The lumen was cleaned by carefully flushing each segment with Krebs' solution using plastic transfer pipets. Segments were transferred to a separate Petri dish containing fresh Krebs' solution and suture threads were tied to both ends of each segment. Tissues were suspended longitudinally using surgical suture, one end attached to the transducer on the top and the other to the tissue holder at the bottom of 20 ml organ bath chambers containing Krebs' solution, maintained at 37° C. with 95% O2 and 5% $CO_2$. Isometric tensions were continuously measured using calibrated force displacement transducers and data was collected and processed by the MP100WSW system with AcqKnowledge software Experiment Protocol Segments of colon were initially loaded to a tension of 2 g and allowed to equilibrate for a 60 min period. During this period, segments were washed with Krebs' solution at 10 minutes intervals. When the tissues obtained regular and stable contraction patterns, GLP-2 agonist response experiments were conducted by the addition of eight concentrations of compound into eight separate organ baths for 5-10 minutes. Routinely, one-hour washes were interspersed between repeat applications of compounds to allow for recovery. The effect of GLP-2(3-33) on GLP-2 agonist analogues were conducted by pre-incubating colon segments with 1 or 10 μM GLP-2(3-33) for 5-10 minutes. Then agonist responses were measured at various concentrations as described above.

Data Analysis

Tension was measured by changes in peak height. Data were calculated and expressed as percentage response relative to the basal level (prior to the experiment). Graphs and $IC_{50}$ determinations were plotted by the percentage response in GraphPad Prism (v 3.02). In order to assess the significance of the effect of GLP-2 and Teduglutide paired t-tests were conducted on the Log [$IC_{50}$] values.

REFERENCES

1. Xiao Q., Boushey R. P., Drucker D. J., Brubaker P. L. Secretion of the intestinotrophic hormone glucagon-like peptide 2 is differentially regulated by nutrients in humans. Gastroenterol. 1999; 117:99-105
2. Drucker D. J., Ehrlich P., Asa S. L., Brubaker P. L. Induction of intestinal epithelial proliferation by glucagon-like peptide-2. Proc. Natl. Acad. Sci. USA 1996; 93:7911-16
3. Tsai C.-H., Hill M., Drucker D. J. Biological determinants of intestinotrophic properties of GLP-2 in viva. Am. J. Physiol. 1997; 272:828-32
4. Tsai C. H., Hill M., Asa S. L., Brubaker P. L., Drucker D. J. Intestinal growth-promoting properties of glucagon-like peptide-2 in mice. Am. J. Physiol. 1997; 273:E77-84
5. Brubaker P. L., Izzo A., Hill M., Drucker D. J. Intestinal function in mice with small bowel growth induced by glucagon-like peptide-2. Am. J. Physiol. 1997; 272: E1050-8
6. Benjamin M. A., McKay D. M., Yang P.-C., Cameron H., Perdue, M H. Glucagon-like peptide-2 enhances intestinal epithelial barrier function of both transcellular and paracellular pathways in the mouse. Gut 2000; 47:112-9
7. Wojdemann M., Wettergren A., Hartmann B., Holst J. J. Glucagon-like peptide-2 inhibits centrally induced antral motility in pigs. Scand. J. Gastroenterol. 1998; 33:828-32
8. Wojdemann M., Wettergren A., Hartmann B., Hilsted L., Holst J. J. Inhibition of sham feeding-stimulated human gastric acid secretion by glucagon-tike peptide-2. J. Clin. Endocrinol. Metab. 1999; 84:2513-17
9. Guan X., Stoll B., Lu X., Tappenden K. A., Hoist J. J., Hartmann B., Burrin D.GLP-2-Mediated Up-Regulation of Intestinal Blood Flow and Glucose Uptake Is Nitric Oxide-Dependent in TPN-Fed Piglets. Gastroenterol. 2003; 125: 136-147
10. Cheeseman C. I., Tsang R. The effect of gastric inhibitory polypeptide and glucagon like peptides on intestinal hexose transport. Am. J. Physiol. 1996; 271:G477-G482
11. Cheeseman, C. I. Upregulation of SGLT-1 transport activity in rat jejunum induced by GLP-2 infusion in vivo. Am. J. Physiol. 1997; 273:R1965-R1971
12. Scott R. B., Kirk D., MacNaughton W. K., Medding J. B. GLP-2 augments the adaptive response to massive intestinal resection in rat. Am. J. Physiol. 1998; 38:G911-21
13. Sigalet D. L., Martin G. R. Hormonal therapy for short bowel syndrome. J. Pediatr. Surg. 2000; 35:360-4
14. Chance W. T., Foley-Nelson T., Thomas I., Balasubramaniam A. Prevention of parenteral nutrition-induced gut hypoplasia by coinfusion of glucagon-like peptide-2. 1997; 273:G559-63
15. Chance W. T., Sheriff S., Foley-Nelson T., Thomas I., Balasubramaniam, A. Maintaining gut integrity during parenteral nutrition of tumor-bearing rats: effects of glucagon-like peptide 2. Nutrition and Cancer 2000; 37:215-22
16. Boushey R., Yusta B., Drucker D. J. GLP-2 decreases mortality and reduces the severity of indomethacin-induced murine enteritis. Am. J. Physiol. 1999; 277:E937-47
17. Drucker D. J., Yusta B., Boushey R. P., DeForest L., Brubaker P. L. Human [Gly2]GLP-2 reduces the severity of colonic injury in a murine model of experimental colitis. Am. J. Physiol. 1999; 276:G79-91
18. Boushey R. P., Yusta B., Drucker D. J. Glucagon-like peptide (GLP)-2 reduces chemotherapy-associated mortality and enhances survival in cells expressing a transfected GLP-2 receptor. Cancer Res. 2001; 61:687-93
19. Tavakkolizadeh A., Shen R., Abraham P., Kormi N., Seifert P., Edelman E. R., et al. Glucagon-like peptide 2: A new treatment for chemotherapy-induced enteritis. J. Surg. Res. 2000; 91:77-82
20. Monroe D. G., Gupta A. K., Kooshesh P., Vyas T. B., Rizkalla G., Wang H., et al. Prototypic G protein-coupled receptor for the intestinotrophic factor glucagon-like peptide-2. Proc. Natl. Acad. Sci. USA 1999; 96:1569-73
21. Yusta B. Somwar R., Wang F., Munroe D., Grinstein S., Klip A., et al. Identification of glucagon-like peptide-2 (GLP-2)-activated signaling pathways in baby hamster kidney fibroblasts expressing the rat GLP-2 receptor. J. Biol. Chem. 1999; 274:30459-67
22. Yusta B., Boushey R. P., Drucker D. J. The glucagon-like peptide-2 receptor mediates direct inhibition of cellular apoptosis via a cAMP-dependent protein kinase-independent pathway. J. Biol. Chem. 2000; 275: 35345-52
23. Walsh, N. A., Yusta, B., DaCambra, M. P., Mini, Y., Drucker, D. J., Brubaker, P. L. Glucagon-like peptide-2 receptor activation in the rat intestinal mucosa. Endocrinology 2003;144(10):4385-92

24. Lovshin, J. A., Huang, Q., Seaberg, R., Brubaker, P. L., Drucker, D. J. Extrahypothalamic Expression of the Glucagon-like Peptide-2 (GLP-2) Receptor is Coupled to Reduction of Glutamate-induced Cell Death in Cultured Hippocampal Cells. Endocrinology 2004; 145: 3495-506

25. Burrin D. G., Stoll B., Jiang R., Petersen Y., Elnif J., Buddington R. K. et al. GLP-2 stimulates intestinal growth in premature TPN-fed pigs by suppressing proteolysis and apoptosis. Am. J. Physiol. 2000; 279: G1249-56

26. Kouris G. J., Rossi Q. L., Djuricin G., Nathan G. C. Weinstein R. A., Prinz R. A. The Effect of Glucagon-like Peptide 2 on Intestinal Permeability and Bacterial Translocation in Acute Necrotizing Pancreatitis. Am. J. Surg. 2001; 181:571-575

27. Prasad R., Alavi K., Schwartz M Z. Glucagon-like peptide-2 analogue enhances intestinal mucosal mass after ischemia and reperfusion. J. Pediatr. Surg. 2000; 35:357-9

28. Prasad R., Alavi K., Schwartz M Z. GLP-2 accelerates recovery of mucosal absorptive function after ischemia/reperfusion. J. Pediatr. Surg. 2001; 36: 570-572

29. Alavi K., Schwartz Z., Palazzo J. P., Prasad R. Treatment of inflammatory bowel disease in a rodent model with the intestinal growth factor glucagon-like peptide-2. J. Ped. Surg. 2000; 35:847-51

30. Cameron H., Yang P.-C, Perdue M. H. Glucagon-like Peptide-2-enhanced Barrier Function Reduces Pathophysiology in a Model of Food Allergy. Am. J. Physiol. 2003; 284: G905-0912

31. Ramsanahie A. P., Perez A., Duensing A. U., Zinner M. J., Ashley S. W., Wang E. E. Glucagon-like peptide 2 enhances intestinal epithelial restitution. J Surg Res 2002; 107: 44-9

We claim:

1. A method for determining a relative ability of different compounds to potentially modulate glucagon-like peptide-2 (GLP-2) receptor activity in intestine comprising the steps of:
   i. incubating a first ex vivo intestinal tissue segment with a GLP-2 receptor ligand;
   ii. taking a first measurement of contractility of the first ex vivo intestinal tissue segment;
   iii. incubating the first ex vivo intestinal tissue segment with the GLP-2 receptor ligand and a first compound;
   iv. taking a second measurement of contractility of the first ex vivo intestinal tissue segment;
   v. incubating a second ex vivo intestinal tissue segment with the GLP-2 receptor ligand;
   vi. taking a first measurement of contractility of the second ex vivo intestinal tissue segment;
   vii. incubating the second ex vivo intestinal tissue segment with the GLP-2 receptor ligand and a second compound;
   viii. taking a second measurement of contractility of the second ex vivo intestinal tissue segment; and
   ix. comparing a difference between the first and the second measurements of contractility of the first ex vivo intestinal tissue segment with a difference between the first and second measurements of contractility of the second ex vivo intestinal tissue segment;
wherein a result of comparing the difference between the first and second measurements of contractility of the first ex vivo intestinal tissue segment with the difference between the first and second measurements of contractility of the second ex vivo intestinal tissue segment is indicative of the relative abilities of the compounds to potentially modulate GLP-2 receptor activity.

2. A method according to claim 1, wherein the intestinal tissue segments are of mammalian origin.

3. A method according to claim 2, wherein the intestinal tissue segments are of human origin.

4. A method according to of claim 2, wherein the intestinal tissue segments are of rat origin.

5. A method according to claim 1, wherein the intestinal tissue segments are independently selected from the group consisting of duodenum, jejunum, ileum, small intestine, and colon.

6. A method according to claim 1, wherein at least one of the compounds is a small molecule.

7. A method according to claim 1, wherein at least one of the compounds is a peptide or peptide analog.

8. A method according to claim 1, wherein the first ex vivo intestinal tissue segment and the second ex vivo intestinal tissue segment are chosen from a first region and a second region of the intestine selected from the group consisting of duodenum, jejunum, ileum, small intestine, and colon, and wherein the first region is a different region of the intestine than the second region.

9. A method according to claim 8, wherein a result of comparing the difference between the first and second measurements of contractility of the first ex vivo intestinal tissue segment with the difference between the first and second measurements of contractility of the second ex vivo intestinal tissue segment is indicative of the relative abilities of the compounds to potentially modulate GLP-2 receptor activity in the first region relative to the second region of the intestine.

10. A method for determining a relative ability of compounds that potentially modulate glucagon-like peptide-2 (GLP-2) receptor activity in intestine comprising the steps of:
    i. incubating an ex vivo intestinal segment with a GLP-2 receptor ligand;
    ii. taking a first measurement of contractility of the ex vivo intestinal tissue segment;
    iii. incubating the ex vivo intestinal tissue segment with the GLP-2 receptor ligand and a first compound;
    iv. taking a second measurement of contractility of the ex vivo intestinal tissue segment;
    v. incubating the ex vivo intestinal tissue segment with the GLP-2 receptor ligand and a second compound; and
    vi. taking a third measurement of contractility of the ex vivo intestinal tissue segment;
wherein a result of a comparison between a difference between the first and second measurements of contractility and a difference between the first and third measurements of contractility is indicative of the relative ability of the first compound and the second compound to potentially modulate the GLP-2 receptor.

11. A method according to claim 10, wherein the ex vivo intestinal tissue segment is of mammalian origin.

12. A method according to claim 11, wherein the ex vivo intestinal tissue segment is of human origin.

13. A method according to of claim 11, wherein the ex vivo intestinal tissue segment is of rat origin.

14. A method according to claim 10, wherein the ex vivo intestinal tissue segment is selected from the group consisting of duodenum, jejunum, ileum, small intestine, and colon.

15. A method according to claim 10, wherein at least one of the compounds is a small molecule.

16. A method according to claim 10, wherein at least one of the compounds is a peptide or peptide analog.

* * * * *